(12) United States Patent
Schuman

(10) Patent No.: US 6,904,915 B2
(45) Date of Patent: Jun. 14, 2005

(54) DEVICE AND METHOD FOR STABILIZING WRISTS AND ARMS

(76) Inventor: Michael Schuman, 15180 Briar Ridge Cir., Ft. Myers, FL (US) 33912

( * ) Notice: Subject to any disclaimer, the term of this patent is extended or adjusted under 35 U.S.C. 154(b) by 360 days.

(21) Appl. No.: 10/057,313

(22) Filed: Jan. 25, 2002

(65) Prior Publication Data

US 2002/0147419 A1 Oct. 10, 2002

Related U.S. Application Data

(60) Provisional application No. 60/264,523, filed on Jan. 26, 2001.

(51) Int. Cl.[7] .................................................. A61F 5/37
(52) U.S. Cl. ........................ 128/878; 128/879; 128/880; 602/21; 602/64
(58) Field of Search ................................ 128/878, 879, 128/880; 602/20, 21, 63, 75, 64, 22, 62; 2/16

(56) References Cited

U.S. PATENT DOCUMENTS

| 4,149,532 | A |   | 4/1979 | Terry et al. |
|---|---|---|---|---|
| 4,953,568 | A | * | 9/1990 | Theisler ..................... 128/878 |
| 4,996,979 | A | * | 3/1991 | Grim et al. ................... 602/21 |
| 5,771,901 | A | * | 6/1998 | O'Brien ..................... 128/878 |
| 5,891,079 | A |   | 4/1999 | Barnes |
| 6,102,880 | A |   | 8/2000 | Nelson et al. |
| 6,126,625 | A |   | 10/2000 | Lundberg |
| 6,341,376 | B1 | * | 1/2002 | Smerdon, Jr. ................ 2/16 |
| 6,482,168 | B1 | * | 11/2002 | Betcher ..................... 602/21 |
| 6,561,995 | B1 | * | 5/2003 | Thibodo, Jr. ................ 602/22 |

* cited by examiner

Primary Examiner—Fadi H. Dahbour
(74) Attorney, Agent, or Firm—Laura G. Barrow

(57) ABSTRACT

A novel device and method for minimizing lateral hand and arm tremors in individuals is disclosed. The device is effective in minimizing tremors in patients suffering from Parkinson's Disease as well as other neurological or drug-induced conditions.

22 Claims, 3 Drawing Sheets

DEVICE AND METHOD FOR STABILIZING WRISTS AND ARMS

This is application claims the benefit of the filing of U.S. provisional application Ser. No. 60/264,523, filed Jan. 26, 2001, which is incorporated by reference herein in its entirety.

BACKGROUND AND SUMMARY OF INVENTION

Between one and one and half million people have been diagnosed with Parkinson's Disease in the United States. As Parkinson's Disease progresses, many sufferers develop tremors in their hands and arms, thereby making common activities such as drinking from a glass, writing, and holding objects difficult if not impossible. The present invention is directed to an arm brace designed to minimize the effects of tremors on people suffering from Parkinson's Disease and other neurological or drug-induced conditions.

DETAILED DESCRIPTION OF PREFERRED EMBODIMENTS

Figure 1:
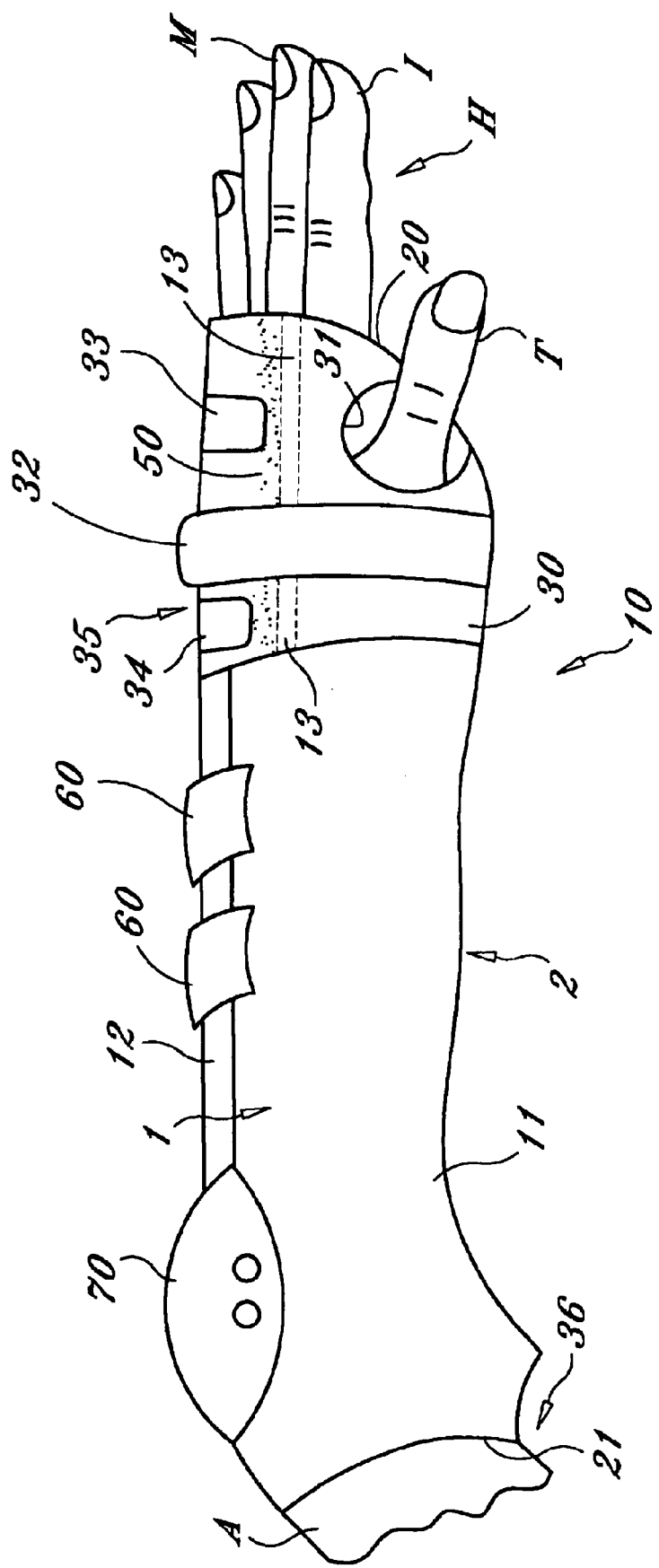
FIG. 1 is a side view of the inventive brace.

Referring now to the figures, the present invention is directed to an arm brace (10) that is useful in minimizing the effects of arm and hand tremors in patients suffering from neurological disorders, such as Parkinson's Disease or drug-induced disorders that cause tremors of the extremities. Specifically, in certain embodiments, the inventive brace comprises a sleeve (11) designed to be worn around the wrist and forearm of a person in need of the brace. The sleeve (11) of the brace (10) may be formed of any material typically used in athletic and orthotic braces, including, but not limited to, leather, neoprene, or cloth. Preferably, an elastomeric material is incorporated within the sleeve to provide a snug, yet comfortable, fit around the person's forearm and wrist.

The sleeve comprises a distal end (20) and proximal end (21), the proximal end (21) having an opening through which a person inserts his/her arm (A). The arm is inserted through the sleeve until the hand (H) exits the distal end of the sleeve and is engaged within the hand portion. Extending distally from the proximal end of the sleeve is a wrist portion (35), followed by a hand portion (30). The hand portion (30) of the sleeve extends around the posterior or back portion of the hand (H) and the anterior or palm portion of the hand (H). The hand portion (30) further includes an opening (31) through which the person's thumb (T) is inserted, as shown most clearly in FIG. 1.

Figure 2:
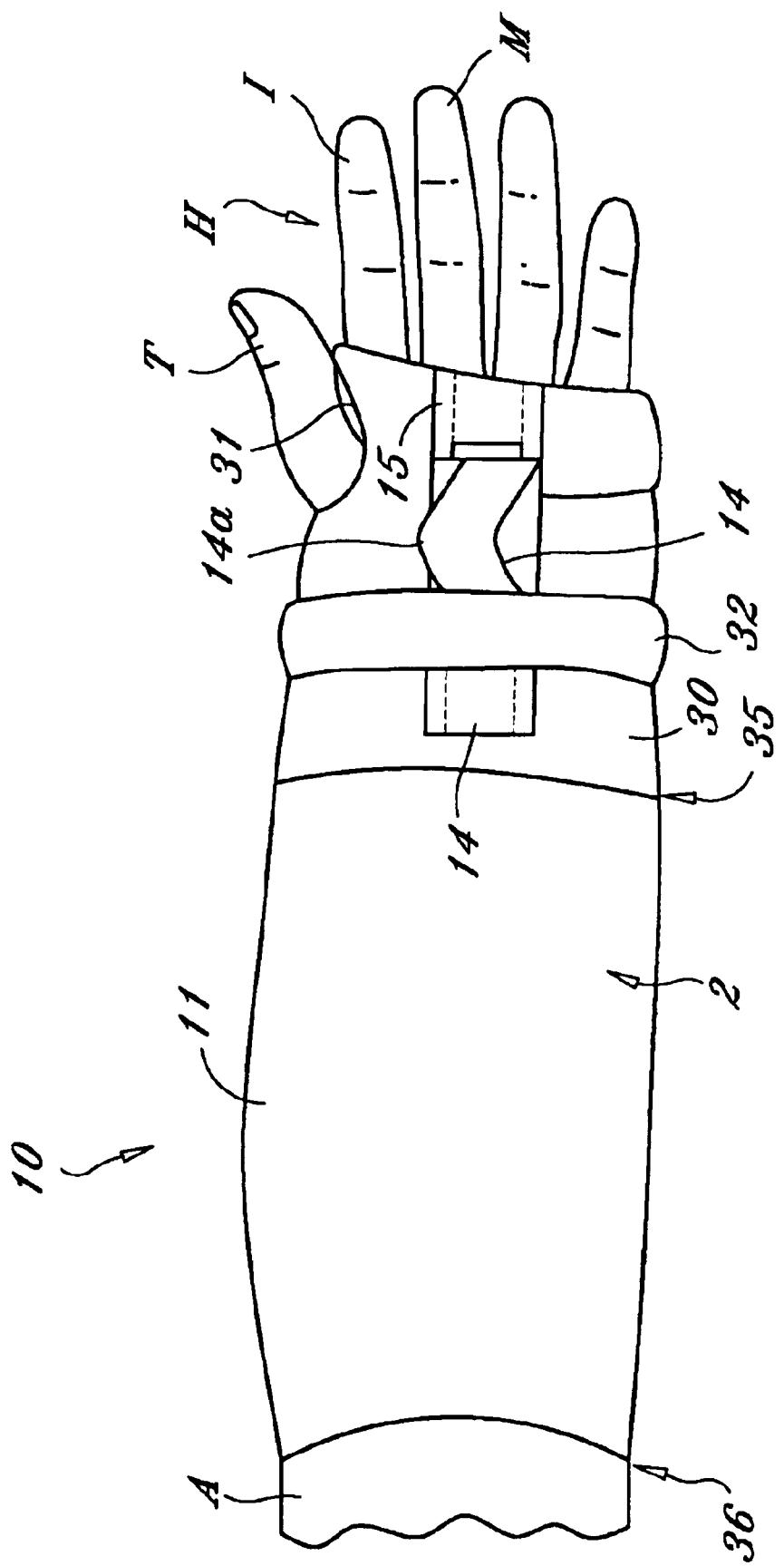
FIG. 2 is an anterior view of the inventive brace.
Figure 3:
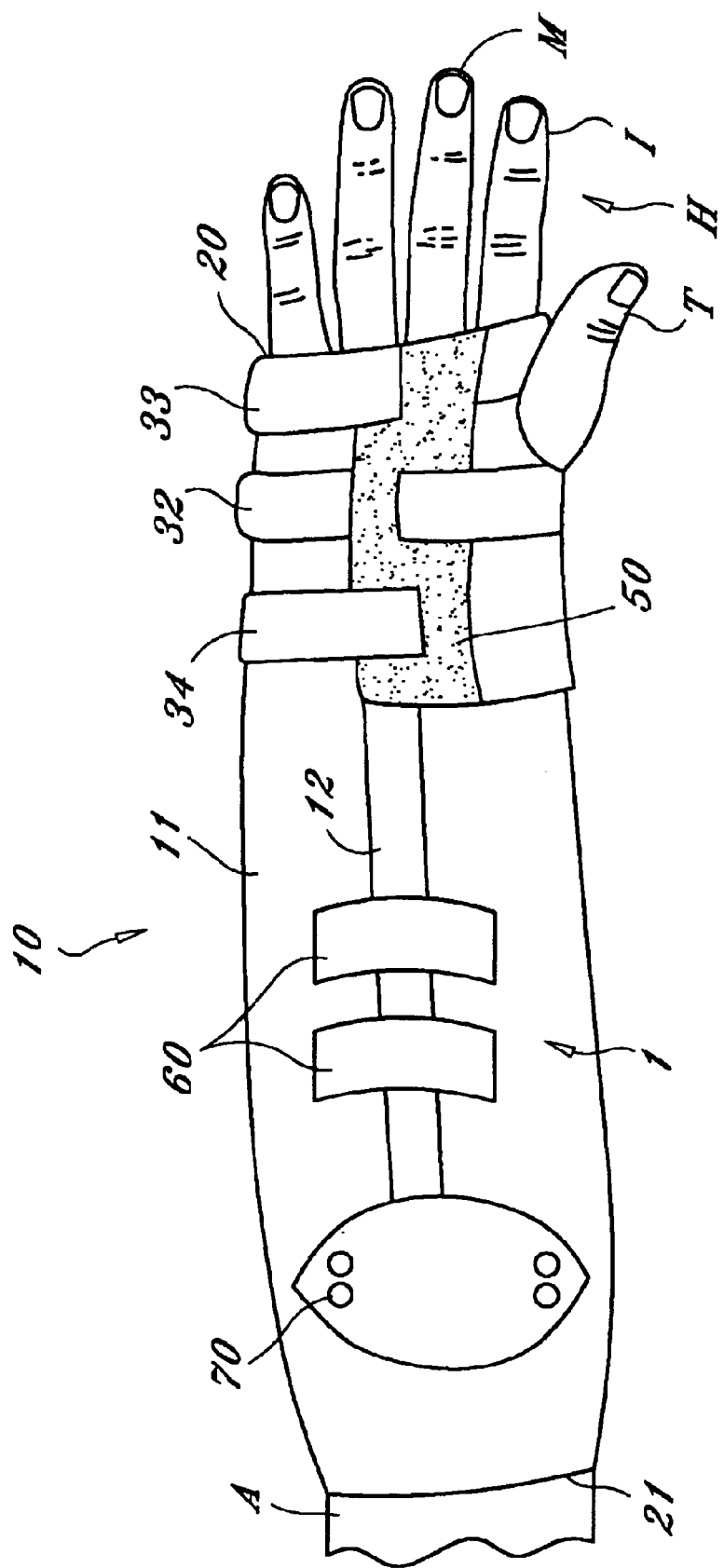
FIG. 3 is a posterior view of the inventive brace.

The brace (10) may further include at least one strap (32) extending from the hand or wrist portions (30, 35) to secure the hand portion more snugly around the person's hand (H). The strap is oriented perpendicularly to the support members (12–14) (discussed below) and configured to circumferentially wrap around the hand or wrist portions. The brace may also include additional straps (33, 34), as shown, to secure the sleeve around the person's hand and forearm. The straps (32–34) may be fastened to the outer surface of the sleeve by means of VELCRO, snaps, or other suitable fastening means. FIGS. 2–3 illustrate the use of a VELCRO strip (50) secured to the sleeve and the straps.

The brace (10) includes a series of elongated support bars (12–14), each of which is secured to the sleeve. [Alternative elongated members, such as rods, for example, may be employed; however, for ease of explanation, reference to this feature of the invention will be made to bars.] The support bars (12–14) may be formed of any suitable, non-flexible material, such as a stiff metal, metal alloy, or plastic, for example. Preferably, one bar (12) is secured to the posterior side (1) of the sleeve. This bar (12) extends from the wrist portion (35) of the sleeve and terminates near the elbow portion (i.e. distal end) (36) of the sleeve. A smaller second elongated bar (14) is preferably secured to the sleeve along the anterior portion (2) of the sleeve. The second bar (14) extends from the distal end (20) of the sleeve comprising the hand portion (30) and terminates proximally just above the wrist portion (35) of the sleeve. The second bar may include a small, elevated contoured section (14a) to accommodate the base of the person's palm. The brace may further include a third elongated bar (13) (shown in phantom in FIG. 1) positioned on the posterior side (1) of the sleeve along the hand portion (30). The third bar (13) extends from the edge of the distal end of the sleeve and terminates near the wrist portion (35) of sleeve. This third bar (13) is preferably positioned along the sleeve such that it is longitudinally aligned with the wearer's index finger (I), middle finger (M), or between the index and middle fingers. Alternatively, the posterior support bars (12,13) comprise a single, integral bar or they may be hingedly connected. The positioning of the three support bars (12–14) allows for some wrist flexibility while simultaneously minimizing the effects of the person's arm tremors, in particular lateral tremors, caused by neurological (e.g. Parkinson's Disease, cerebral palsy) or drug-induced conditions. Optionally, the brace may include an outer elbow pad or shield (70).

Certain aspects of the inventive brace include a sleeve formed of a washable fabric. In this embodiment, it may be desirable to provide support bars, as described and illustrated herein, that are removable. Alternatively, the support bars may be permanently secured to the sleeve. FIGS. 1 and 3 illustrate the use of straps (60) for holding the larger support bar (12) in place on the exterior surface of the sleeve (11). Alternatively, the support bars may be housed within a compartment sewn into or attached to the sleeve. In FIG. 3, for example, a compartment (15) is secured to the outer surface of the sleeve and configured to house most of the anterior support bar (14) (partially shown in phantom) with only the convex section (14a) of the bar exposed. The inventive brace may be fabricated in different sizes for use on either arm. Alternatively, separate left-arm and right-arm braces may be designed.

The inventor of the present invention tested his invention on six individuals suffering from Parkinson's Disease. The results of the study are discussed in Example 1.

EXAMPLE 1

Six patients suffering from Parkinson's Disease were each given a container holding 15 ml of water. Without wearing the inventive brace, each patient was first asked to hold the water-filed container. The amount of water that spilled out the container due to the patient's arm and/or hand tremors was measured. Each patient was then asked to the hold the water-filed container while wearing the inventive brace. The amount of water that spilled out of the container due to the patient's arm and/or hand tremors was measured. The amounts of water spilled from the container with the brace verses without the brace were compared, as shown in Table 1.

TABLE 1

|  | Without Brace | With Brace |
|---|---|---|
| Patient 1 | 7.5 ml | 5 ml |
| Patient 2 | 7.2 ml | 4.5 ml |
| Patient 3 | 10 ml | 2.5 ml |
| Patient 4 | 5 ml | 0 ml |
| Patient 5 | 7 ml | 0 ml |
| Patient 6 | 6 ml | 4 ml |

I claim:

1. An arm brace comprising:
   a. a sleeve having an proximal end, a distal end, an anterior surface, and a posterior surface;
   b. said sleeve further having an opening at said proximal end through which an arm may be inserted, a wrist portion positioned distally from said proximal opening, and a hand portion positioned distally from said wrist portion and including said distal end, said hand portion further having a first opening through which a hand of said arm is engaged;
   c. a first elongated support member secured to said posterior surface of said sleeve, said first member extending distally from near said proximal end of said sleeve and terminating distally near said wrist portion;
   d. a second elongated member secured to said anterior surface of said sleeve, said second elongated member extending from said wrist portion of said sleeve to said distal end of said sleeve; and
   e. a third elongated support member secured to said posterior surface of sleeve, said third member extending distally from said first member near said wrist portion of said sleeve and terminating near said distal end of said sleeve.

2. The arm brace of claim 1, further including at least one strap secured to said hand or wrist portions of said sleeve, said at least one strap oriented perpendicularly to said elongated members and configured to circumferentially wrap around said hand or wrist portions of said sleeve upon engagement of said arm and hand within said sleeve.

3. The arm brace of claim 1, wherein said first and third elongated members comprise a single, integral member.

4. The arm brace of claim 1, wherein said first and third elongated members are hingedly secured to one another.

5. The arm brace of claim 2, wherein said first and third elongated members comprise a single, integral member.

6. The arm brace of claim 2, wherein said first and third elongated members are hingedly secured to one another.

7. An arm brace comprising:
   a. a sleeve having an proximal end, a distal end, an anterior surface, and a posterior surface;
   b. said sleeve further having an opening at said proximal end through which an arm may be inserted, a wrist portion positioned distally from said proximal opening, and a hand portion positioned distally from said wrist portion and including said distal end, said hand portion further having a first opening through which a hand of said arm is engaged;
   c. a first elongated support member secured to said posterior surface of said sleeve, said first member extending distally from near said proximal end of said sleeve and terminating distally near said wrist portion;
   d. a second elongated member secured to said anterior surface of said sleeve, said second elongated member extending from said wrist portion of said sleeve to said distal end of said sleeve;
   e. said hand portion further having a second opening positioned between said anterior and posterior surfaces of said sleeve, said second opening configured to engage a thumb of said hand engaged within said hand portion;
   f. at least one strap secured to said hand or wrist portions of said sleeve, said at least one strap oriented perpendicularly to said elongated members and configured to circumferentially wrap around said hand or wrist portions of said sleeve upon engagement of said arm and hand within said sleeve; and
   g. a third elongated support member secured to said posterior surface of sleeve, said third member extending distally from said first member near said wrist portion of said sleeve and terminating near said distal end of said sleeve.

8. The arm brace of claim 7, wherein said first and third elongated members comprise a single, integral member.

9. The arm brace of claim 7, wherein said first and third elongated members are hingedly secured to one another.

10. The arm brace of claim 7, said brace further including an elbow shield secured to said posterior surface of said sleeve near said proximal end of said sleeve.

11. A method for minimizing hand and arm tremors in individuals suffering from a medical condition causing said tremors, said method comprising attaching an arm brace to of an individual's arm, wherein said brace comprises:
   a. a sleeve having an proximal end, a distal end, an anterior surface, and a posterior surface;
   b. said sleeve further having an opening at said proximal end through which an arm may be inserted, a wrist portion positioned distally from said proximal opening, and a hand portion positioned distally from said wrist portion and including said distal end, said hand portion further having a first opening through which a hand of said arm is engaged;
   c. a first elongated support member secured to said posterior surface of said sleeve, said first member extending distally from near said proximal end of said sleeve and terminating distally near said wrist portion;
   d. a second elongated member secured to said anterior surface of said sleeve, said second elongated member extending from said wrist portion of said sleeve to said distal end of said sleeve; and
   e. a third elongated support member secured to said posterior surface of sleeve, said third member extending distally from said first member near said wrist portion of said sleeve and terminating near said distal end of said sleeve.

12. The method of claim 11, further including at least one strap secured to said hand or wrist portions of said sleeve, said at least one strap oriented perpendicularly to said elongated members and configured to circumferentially wrap around said hand or wrist portions of said sleeve upon engagement of said arm and hand within said sleeve.

13. The method of claim 11, wherein said first and third elongated members comprise a single, integral member.

14. The method of claim 11, wherein said first and third elongated members are hingedly secured to one another.

15. The method of claim 12, wherein said first and third elongated members comprise a single, integral member.

16. The method of claim 12, wherein said first and third elongated members are hingedly secured to one another.

17. The method of claim 11, said brace further including an elbow shield secured to said posterior surface of said sleeve near said proximal end of said sleeve.

18. A method for minimizing hand and arm tremors in individuals suffering from a medical condition causing said tremors, said method comprising attaching an arm brace to an individual's arm, wherein said brace comprises:
   a. a sleeve having an proximal end, a distal end, an anterior surface, and a posterior surface;
   b. said sleeve further having an opening at said proximal end through which an arm may be inserted, a wrist portion positioned distally from said proximal opening, and a hand portion positioned distally from said wrist portion and including said distal end, said hand portion further having a first opening through which a hand of said arm is engaged;
   c. a first elongated support member secured to said posterior surface of said sleeve, said first member extending distally from near said proximal end of said sleeve and terminating distally near said wrist portion;
   d. a second elongated member secured to said anterior surface of said sleeve, said second elongated member extending from said wrist portion of said sleeve to said distal end of said sleeve;
   e. said hand portion further having a second opening positioned between said anterior and posterior surfaces of said sleeve, said second opening configured to engage a thumb of said hand engaged within said hand portion;
   f. at least one strap secured to said hand or wrist portions of said sleeve, said at least one strap oriented perpendicularly to said elongated members and configured to circumferentially wrap around said hand or wrist portions of said sleeve upon engagement of said arm and hand within said sleeve; and
   g. a third elongated support member secured to posterior surface of sleeve, said third member extending distally from said first member near said wrist portion of said sleeve and terminating near said distal end of said sleeve.

19. The method of claim 18, wherein said first and third elongated members comprise a single, integral member.

20. The method of claim 18, wherein said first and third elongated members are hingedly secured to one another.

21. The method of claim 18, said brace further including an elbow shield secured to said posterior surface of said sleeve near said proximal end of said sleeve.

22. An arm brace comprising:
   a. a sleeve having an proximal end, a distal end, an anterior surface, and a posterior surface;
   b. said sleeve further having an opening at said proximal end through which an arm may be inserted, a wrist portion positioned distally from said proximal opening, and a hand portion positioned distally from said wrist portion and including said distal end, said hand portion further having a first opening through which a hand of said arm is engaged;
   c. a first elongated support member secured to posterior surface of said sleeve, said first member extending distally from near said proximal end of said sleeve and terminating distally near said wrist portion;
   d. a second elongated member secured to said anterior surface of said sleeve, said second elongated member extending from said wrist portion of said sleeve to said distal end of said sleeve; and
   e. an elbow shield secured to said posterior surface of said sleeve near said proximal end of said sleeve.

* * * * *